United States Patent
Hitce et al.

(10) Patent No.: US 10,357,440 B2
(45) Date of Patent: Jul. 23, 2019

(54) COMPOSITION COMPRISING AT LEAST ONE 2-(3,4-DISUBSTITUTED)PHENYL-1-(3,4-DISUBSTITUTED)PHENYL-1-HYDROXYETHANE FOR PREVENTING AND/OR TREATING THE SIGNS OF AGEING OF THE SKIN

(71) Applicant: L'OREAL, Paris (FR)

(72) Inventors: Julien Hitce, Aulnay-sous-Bois (FR); Maria Dalko, Versailles (FR); Marie-Céline Frantz, Aulnay-sous-Bois (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/538,988

(22) PCT Filed: Dec. 21, 2015

(86) PCT No.: PCT/EP2015/080804
§ 371 (c)(1),
(2) Date: Jun. 22, 2017

(87) PCT Pub. No.: WO2016/102475
PCT Pub. Date: Jun. 30, 2016

(65) Prior Publication Data
US 2017/0367952 A1 Dec. 28, 2017

(30) Foreign Application Priority Data
Dec. 22, 2014 (FR) ..................... 14 63069

(51) Int. Cl.
*A61K 31/05* (2006.01)
*A61K 8/34* (2006.01)
*A61K 8/33* (2006.01)
*A61Q 19/08* (2006.01)
*C07C 43/23* (2006.01)

(52) U.S. Cl.
CPC ............... *A61K 8/347* (2013.01); *A61K 8/33* (2013.01); *A61Q 19/08* (2013.01); *C07C 43/23* (2013.01)

(58) Field of Classification Search
CPC .................................... A61K 31/05
USPC ...................................... 514/734
See application file for complete search history.

(56) References Cited

U.S. PATENT DOCUMENTS

| | | |
|---|---|---|
| 2001/0025056 A1 | 9/2001 | Maignan |
| 2003/0144363 A1 | 7/2003 | Liviero et al. |
| 2005/0267047 A1 | 12/2005 | Jia et al. |
| 2006/0003919 A1 | 1/2006 | Fortunel et al. |

FOREIGN PATENT DOCUMENTS

| | | |
|---|---|---|
| JP | 2001-058916 A | 3/2001 |
| JP | 2001-253820 A | 9/2001 |
| JP | 2007-153863 A | 6/2007 |
| JP | 2008-501030 A | 1/2008 |
| JP | 2009-132678 A | 6/2009 |
| WO | 2012/149608 A1 | 11/2012 |
| WO | WO 14/048868 * | 4/2014 |

OTHER PUBLICATIONS

Jordan, V. C. Nature Reviews: Drug Discovery, 2, 2003, 205.*
Vippagunta, et al. Advanced Drug Delivery Reviews, 48, 2001, 18.*

* cited by examiner

*Primary Examiner* — Douglas M Willis
(74) *Attorney, Agent, or Firm* — Oliff PLC

(57) ABSTRACT

The present invention relates to the cosmetic use, in a composition containing a physiologically acceptable medium, of at least one compound of formula (I) in which: —$R_3$ means a hydrogen atom or a hydroxyl radical, —$R_1$ and $R_2$ mean, independently of each other, a hydrogen atom, a linear or branched C1-C6 alkyl radical; a benzyl radical; a linear or branched C1-C6 alkylcarbonyl radical not conjugated with the carbonyl; or a linear or branched C1-C6 alkoxycarbonyl radical, and/or of an isomer and/or of a salt and/or of a solvate of said compound of formula (1), for preventing and/or treating the signs of ageing of the skin and its appendages.

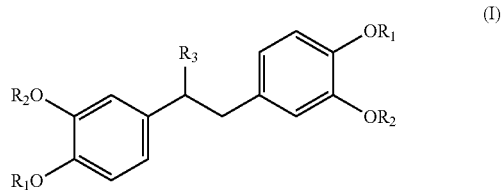

(I)

16 Claims, No Drawings

COMPOSITION COMPRISING AT LEAST ONE 2-(3,4-DISUBSTITUTED)PHENYL-1-(3,4-DISUBSTITUTED)PHENYL-1-HYDROXYETHANE FOR PREVENTING AND/OR TREATING THE SIGNS OF AGEING OF THE SKIN

The present invention relates to the use of 1-(3,4-disubstituted)phenyl-2-(3,4-disubstituted)phenylethane compounds and to the use thereof especially for inhibiting the glycation of proteins, particularly proteins of the skin, the nails and/or the hair. The invention relates to compositions containing, in a physiologically acceptable medium, at least one 1-(3,4-disubstituted)phenyl-2-(3,4-disubstituted)phenylethane compound as an agent for reducing and/or retarding the signs of ageing of the skin and/or of its appendages, most particularly the hair.

BACKGROUND

Glycation is a non-enzymatic process involving a saccharide (glucose or ribose) which reacts via the Maillard reaction with an amine group of an amino acid residue (for instance lysine), particularly an amino acid residue of a protein, to form a Schiffs base. This base, after an Amadori molecular rearrangement, may lead, via a succession of reactions, to bridging, particularly intramolecular bridging, for instance of pentosidine type.

This phenomenon increases regularly with age. It is characterized by the appearance of glycation products, the content of which increases uniformly as a function of age. Glycation products are, for example, pyrraline, carboxymethyllysine, pentosidine, crossline, Nε(2-carboxyethyl)lysine (CEL), glyoxal-lysine dimer (GOLD), methylglyoxal-lysine dimer (MOLD), 3DG-ARG imidazolone, versperlysines A, B, C, threosidine, or advanced glycosylation end products or AGEs.

The glycation of proteins is thus a universal phenomenon, which is well known as regards the skin, particularly as regards its dermal component, but which also takes place in the skin appendages such as the nails or the hair, particularly on keratins and more generally throughout the protein system, provided that the conditions required for glycation are met.

Human skin is constituted of two compartments, namely an upper compartment, the epidermis, and a deep compartment, the dermis.

Natural human epidermis is composed mainly of three types of cells, namely keratinocytes, which form the vast majority, melanocytes and Langerhans cells. Each of these cell types contributes by virtue of its intrinsic functions to the essential role played in the body by the skin.

The dermis provides the epidermis with a solid support. It is also its nourishing element. It is mainly formed from fibroblasts and an extracellular matrix which is itself composed of various extracellular proteins, among which are especially collagen fibres, elastin and various glycoproteins. All of these extracellular components are synthesized by the fibroblasts. Leukocytes, mastocytes or tissue macrophages are also found in the dermis. Finally, the dermis contains blood vessels and nerve fibres.

Fibroblasts, via their activity in the synthesis of extracellular matrix proteins (proteoglycans, collagen fibres and other structural glycoproteins) are the main actors in the structural development of the dermis.

Collagen fibres give the dermis its solidity. They are very strong, but sensitive to certain enzymes generally known as collagenases. In the dermis, collagen fibres are formed from fibrils sealed together, thus forming more than 10 different types of structures. The structure of the dermis is in large part due to the entanglement of the collagen fibres packed together. The collagen fibres contribute to the tonicity of the skin.

The collagen fibres are regularly renewed, but this renewal decreases with age, which leads especially to thinning of the dermis. It is also accepted that extrinsic factors such as smoking or certain treatments (retinoic acid and derivatives, glucocorticoids, vitamin D and derivatives, for example) also have an effect on the skin and on its collagen content.

As regards the dermal component of the skin, glycation takes place mainly in the dermis, on collagen fibres, according to the process described above. The glycation of collagen increases uniformly with age, leading to a uniform increase in the content of glycation products in the skin.

Without wishing to introduce any theory of ageing of the skin, it should be noted that other changes in collagen might also be a consequence of glycation, such as a decrease in heat denaturation, an increase in resistance to enzymatic congestion and an increase in intermolecular bridging. These effects were able to be demonstrated in the course of ageing of the skin (Tanaka S. et al., 1988, J. Mol. Biol., 203, 495-505; Takahashi M. et al., 1995, Analytical Biochemistry, 232, 158-162). Furthermore, glycation-mediated changes in certain constituents of the basal membrane such as collagen IV, laminin and fibronectin were able to be demonstrated (Tarsio J F. et al., 1985, Diabetes, 34, 477-484; Tarsio J. F. et al., 1988, Diabetes, 37, 532-539; Sternberg M. et al., 1995, C. R. Soc. Biol., 189, 967-985).

It is thus understood that, in the course of ageing of the skin, the physicochemical properties of collagen become modified and collagen becomes more difficult to dissolve and more difficult to degrade.

Thus, one of the components of aged skin clearly appears to be glycated collagen.

It is known that the skin results from a close association between at least two compartments from which it is constituted, namely the epidermis and the dermis. The interactions between the dermis and the epidermis are such that it is reasonable to think that a change in one may have consequences on the other. It may be suspected that ageing of the dermis in particular with its glycation phenomena is bound to have consequences on the epidermis associated therewith. Thus, in the course of ageing of the skin, the glycation of collagen must lead to changes in the epidermis that necessarily contribute towards the ageing of the epidermis.

Thus, if the glycation of dermal proteins, particularly collagen, has so many detrimental consequences in the skin, similar consequences are to be expected of the glycation of proteins in the skin appendages, for instance the nails and/or the hair and, for that matter, of any protein system.

The need for products that reduce the phenomenon of protein glycation may thus be understood.

SUMMARY

In this regard, the Applicant has shown, surprisingly and unexpectedly, that certain 1-(3,4-disubstituted)phenyl-2-(3,4-disubstituted)phenylethane compounds have the property of reducing or inhibiting the phenomenon of protein glycation.

It is known from WO 2012/149608 that stilbene derived compounds can be of use for the treatment of skin aging. However, this document reports the use of compounds comprising phenyl groups that are substituted in a different pattern than the compounds of the invention.

One subject of the present invention is the cosmetic use, in a composition containing a physiologically acceptable medium, of at least one 1-(3,4-disubstituted)phenyl-2-(3,4-disubstituted)phenylethane compound as defined in the present description, or an isomer or a salt or a solvate of said compound, for inhibiting the glycation of skin proteins, especially dermal proteins such as collagen, and/or for inhibiting the glycation of proteins of the skin appendages such as the nails and the hair, for instance keratins.

The present invention relates to the cosmetic use, in a composition containing a physiologically acceptable medium, of at least one 1-(3,4-disubstituted)phenyl-2-(3,4-disubstituted)phenylethane compound as defined in the present description, or an isomer or a salt or a solvate of said compound, for preventing and/or treating the signs of ageing of the skin and/or its appendages, in particular the nails and the hair.

In particular, the 1-(3,4-disubstituted)phenyl-2-(3,4-disubstituted)phenylethanes defined in the present description may be used for cosmetically treating the signs of ageing of the skin, the nails and/or the hair, which includes a cosmetic treatment of the signs of ageing of the skin, the nails and/or the hair associated with protein glycation.

The term "signs of ageing of the skin" means any modification of the outer appearance of the skin due to ageing, whether chronobiological and/or extrinsic, extrinsic ageing mainly being caused by physical or chemical attack by the environment, which is manifested, for example, by wrinkles and fine lines, withered skin, flaccid skin, thinned skin, dull, lifeless skin, or lack of elasticity and/or of tonicity of the skin. For the purposes of the present description, extrinsic ageing is mainly caused by physical or chemical attack by the environment. Physical attack by the environment includes extreme temperatures. Chemical attack by the environment includes contact of the skin and/or its appendages especially with pollutant substances present in atmospheric air.

This term is considered to be equivalent to the term "skin disorders induced by chronological ageing and/or extrinsic ageing".

According to the invention, the term "preventing" or "prevention" means reducing the risk of occurrence or slowing down the occurrence of a given phenomenon, namely, according to the present invention, the signs of ageing of the skin and the signs of ageing of the skin's appendages.

The invention also relates to a composition comprising at least one 1-(3,4-disubstituted)phenyl-2-(3,4-disubstituted) phenylethane compound of formula (I) as defined in the present description.

A composition in accordance with the invention, i.e. which is intended for implementing the invention, may be a cosmetic composition, and may thus comprise a physiologically acceptable medium.

The composition used according to the invention may be administered especially topically or orally.

Advantageously, a composition that is suitable for use in the invention, comprising a 1-(3,4-disubstituted)phenyl-2-(3,4-disubstituted)phenylethane compound of formula (I) in accordance with the invention, is intended for topical administration.

The term "physiologically acceptable medium" means a medium that is compatible with all keratin materials such as the skin, the scalp, the nails, mucous membranes, the eyes and the hair, or any other area of bodily skin. A physiologically acceptable medium is preferentially a cosmetically or dermatologically acceptable medium, which has no unpleasant colour and/or appearance, and which is entirely compatible with the route of administration under consideration.

When the composition is intended to be administered topically, such a medium is considered as being physiologically acceptable when it does not cause any stinging, tautness or redness that is unacceptable to the user.

The invention also relates to a cosmetic process for treating the signs of ageing, especially associated with glycation, of the skin, the nails and/or the hair, characterized in that a cosmetic composition comprising an effective amount of at least one 1-(3,4-disubstituted)phenyl-2-(3,4-disubstituted)phenylethane compound of formula (I) as defined in the present description is applied to the skin, the nails and/or the hair.

Certain 1-(3,4-disubstituted)phenyl-2-(3,4-disubstituted) phenylethane compounds of formula (I), of which the use is defined in the present description, are known. Certain other 1-(3,4-disubstituted)phenyl-2-(3,4-disubstituted)phenylethane compounds of formula (I), of which the use is defined in the present description, are novel compounds which have been specially designed for the purposes of implementing the invention.

Thus, the present invention also relates to certain 1-(3,4-disubstituted)phenyl-2-(3,4-disubstituted)phenylethane compounds of formula (I) defined in the present description, which compounds, to the Applicant's knowledge, have not been described in the prior art.

Likewise, the present invention provides processes for preparing the 1-(3,4-disubstituted)phenyl-2-(3,4-disubstituted)phenylethane compounds of formula (I), of which the use is defined in the present description, including the novel 1-(3,4-disubstituted)phenyl-2-(3,4-disubstituted)phenylethane compounds of formula (Ia) or (Ib).

DETAILED DESCRIPTION OF EMBODIMENTS 1-(3,4-Disubstituted)phenyl-2-(3,4-disubstituted) phenylethane compounds used according to the invention As stated previously, the invention relates generally to the cosmetic use, in a composition containing a physiologically acceptable medium, of at least one compound of formula (I):

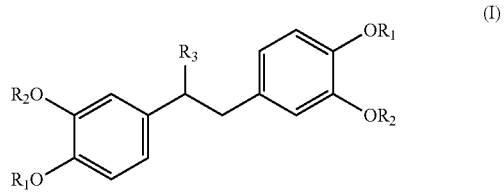

in which:
R$_3$ means a hydrogen atom or a hydroxyl radical,
R$_1$ and R$_2$ mean, independently of each other, a hydrogen atom, a linear or branched C1-C6 alkyl radical; a benzyl radical; a linear or branched C1-C6 alkylcarbonyl radical not conjugated with the carbonyl; or a linear or branched C1-C6 alkoxycarbonyl radical,
and/or of an isomer and/or of a salt and/or of a solvate of said compound of formula (I),
for preventing and/or treating the signs of ageing of the skin and its appendages.

For the purposes of the invention, an alkyl radical is a linear or branched, saturated or unsaturated aliphatic group. A saturated alkyl designates a radical obtained from an alkane wherein one hydrogen is missing. An unsaturated alkyl radical designates a radical obtained from an alkene or an alkyne, comprising respectively at least one double or at least one triple bond between two carbon atoms, wherein one hydrogen is missing. These radicals are also designated as alkenyl or alkynyl groups, respectively. An alkynyl group can further comprise at least one double bond in it structure.

In the sense of the invention, when the alkyl radical is unsaturated, the phrase "the alkylcarbonyl radical is not conjugated with the carbonyl" means that a double bond present in the unsaturated alkyl radical cannot be directly linked to the carbon atom which is adjacent to the carbon atom of the carbonyl function.

A C1-C6 alkyl radical is an alkyl group comprising from 1 to 6 carbon atoms, i.e. the alkyl group may comprise 1, 2, 3, 4, 5 or 6 carbon atoms. Examples of alkyl groups that may be mentioned include methyl, ethyl, propyl, isopropyl, butyl, isobutyl, tert-butyl, pentyl, hexyl, allyl, etc. groups.

For the purposes of the invention, a benzyl radical is an aromatic group of empirical formula C6H5-CH2-R' and of structural formula (X1):

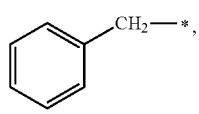
(X1)

For the purposes of the invention, an alkylcarbonyl radical is a group of formula (X2)

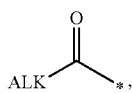
(X2)

in which "Alk" means an alkyl radical as defined above.

When the alkyl is unsaturated, the expression "alkylcarbonyl radical not conjugated with the carbonyl" means that a double bond present in the unsaturated alkyl radical cannot be directly linked to the carbon atom which is adjacent to the carbon atom of the carbonyl function.

For the purposes of the invention, an alkoxy is an —O-alkyl group in which the alkyl radical is as defined previously. A C1-C6 alkoxy radical is an —O-alkyl group in which the alkyl radical comprises from 1 to 6 carbon atoms, i.e. the alkyl group may comprise 1, 2, 3, 4, 5 or 6 carbon atoms. A C1-C6 alkoxy radical includes methoxy, ethoxy, propoxy, butoxy, pentoxy and hexyloxy groups.

For the purposes of the invention, an alkoxycarbonyl group is a group of formula (X3):

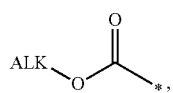
(X3)

in which the "Alk-O" group means an alkoxy radical as defined previously.

Preferably, the isomers according to the invention are stereoisomers, in particular enantiomers, diastereoisomers, and also mixtures thereof, including racemic mixtures.

The acceptable solvates of the compounds of formula (I), (Ia) and (Ib) comprise conventional solvates such as those formed during the last step of the preparation of said compounds due to the presence of solvents. Mention may be made, by way of example, of the solvates due to the presence of water or of linear or branched alcohols, such as ethanol or isopropanol.

The term "salts" designate the conventional ionic compounds, that result from the neutralization reaction of these compounds. Salts are composed of related numbers of cations and anions so that the final product is electrically neutral.

Salts of the compounds of formula (I), (Ia) and (Ib) may be organic salts and/or minerals. They may be chosen from metal salts, for example aluminum ($Al^{3+}$), zinc ($Zn^{2+}$), manganese ($Mn^{2+}$) or copper ($Cu^{2+}$); alkali metal salts, for example lithium ($Li^+$), sodium ($Na^+$) or potassium ($K^+$); and alkaline earth metal salts, for example calcium ($Ca^{2+}$) or magnesium ($Mg^{2+}$). It may also include salts of formula $NH_4^+$ or organic salts of formula $NHX_3^+$, $NX_3$ designating an organic amine, the radicals X being identical or different, two or three X radicals can form in pairs a ring with the nitrogen atom which carries them or $NX_3$ possibly denotes an aromatic amine. Organic amines denote in particular alkylamines, such as methylamine, dimethylamine, trimethylamine, triethylamine or ethylamine; hydroxyalkylamines such as 2-hydroxyethylamine, bis-(2-hydroxyethyl) amine or tri-(2-hydroxyethyl) amine; cycloalkylamines such as bicyclohexylamine or glucamine, piperidine; pyridines and the like, for example collidine, quinine or quinoline; and amino acids with basic character, as for example the lysine or arginine.

Preferably salts compounds of formula (I), (Ia) and (Ib) are calcium salts.

According to a first variant of the invention, the compound of formula (I) is characterized in that:
$R_1$ means a hydrogen atom; a linear or branched C1-C6 alkylcarbonyl radical not conjugated with the carbonyl, or a linear or branched C1-C6 alkoxycarbonyl radical, and
$R_2$ means a linear or branched C1-C6 alkyl radical.

According to a second variant of the invention, the compound of formula (I) is characterized in that:
$R_1$ means a hydrogen atom; and
$R_2$ means a linear or branched C1-C6 alkyl radical, preferably a linear or branched saturated C1-C4 alkyl radical.

According to a third variant of the invention, the compound of formula (I) is characterized in that:
$R_1$ means a hydrogen atom,
$R_2$ means a methyl radical, and
$R_3$ means a hydrogen atom or a hydroxyl radical.

The structural formula of these two particular compounds, referred to in the rest of the text as compounds (A) when $R_3$ means a hydroxyl radical and as compound (B) when $R_3$ means a hydrogen atom, is represented below:

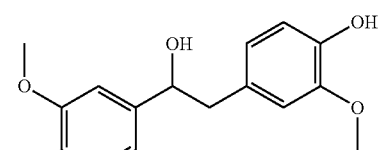
(A)

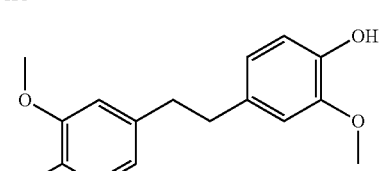
(B)

The present invention also relates to novel chemical compounds of formula (Ia):

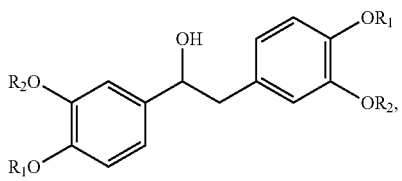

in which the meaning of $R_1$ and $R_2$ is chosen from the following combinations:

A. $R_1$ means a hydrogen atom and $R_2$ means a hydrogen atom; a linear or branched C2-C6 alkyl radical; a benzyl radical; a linear or branched C1-C6 alkylcarbonyl radical not conjugated with the carbonyl; or a linear or branched C1-C6 alkoxycarbonyl radical;

B. $R_1$ means a methyl radical and $R_2$ means a linear or branched C2-C6 alkyl radical; a linear or branched C1-C6 alkylcarbonyl radical not conjugated with the carbonyl; or a linear or branched C1-C6 alkoxycarbonyl radical;

C. $R_1$ means a linear or branched C2-C6 alkyl radical; a benzyl radical; a linear or branched C1-C6 alkylcarbonyl radical not conjugated with the carbonyl; or a linear or branched C1-C6 alkoxycarbonyl radical; and $R_2$ means a hydrogen atom; a linear or branched C1-C6 alkyl radical; a benzyl radical; a linear or branched C1-C6 alkylcarbonyl radical not conjugated with the carbonyl; or a linear or branched C1-C6 alkoxycarbonyl radical, and also the isomers, salts and solvates of this compound of formula (Ia).

The present invention also relates to novel chemical compounds of formula (Ib):

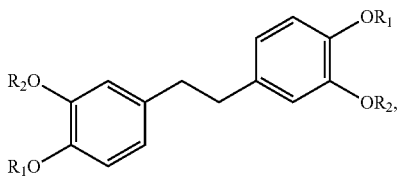

in which the meaning of $R_1$ and $R_2$ is chosen from the following combinations:

A. $R_1$ means a hydrogen atom or an ethyl radical, and $R_2$ means a hydrogen atom; a linear or branched C2-C6 alkyl radical; a benzyl radical; a linear or branched C1-C6 alkylcarbonyl radical not conjugated with the carbonyl; or a linear or branched C1-C6 alkoxycarbonyl radical;

B. $R_1$ means a methyl radical and $R_2$ means a linear or branched C3-C6 alkyl radical; a linear or branched C1-C6 alkylcarbonyl radical not conjugated with the carbonyl; or a linear or branched C1-C6 alkoxycarbonyl radical;

C. $R_1$ means a benzyl radical or an acetyl, and $R_2$ means a hydrogen atom; a linear or branched C2-C6 alkyl radical; a benzyl radical; a linear or branched C1-C6 alkylcarbonyl radical not conjugated with the carbonyl; or a linear or branched C1-C6 alkoxycarbonyl radical;

D. $R_1$ means a linear or branched C3-C6 alkyl radical; a linear or branched C2-C6 alkylcarbonyl not conjugated with the carbonyl; or a linear or branched C1-C6 alkoxycarbonyl radical; and $R_2$ means a hydrogen atom; a linear or branched C1-C6 alkyl radical; a benzyl radical; a linear or branched C1-C6 alkylcarbonyl not conjugated with the carbonyl; or a linear or branched C1-C6 alkoxycarbonyl radical, on the understanding that:

$R_1$ and $R_2$ cannot simultaneously denote a hydrogen atom, or a methyl, allyl, n-butyl, n-pentyl or acetyl radical, and also the isomers, salts and solvates of this compound of formula (Ib).

Synthesis of the Novel Compounds
Common Precursors of Formula (II)
Ethylenic Precursors of Formula (II):

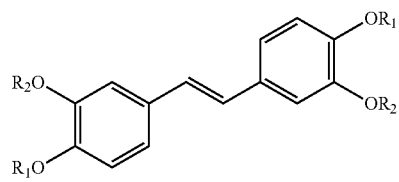

may be obtained in various ways:
either via an olefination of Wittig type and variants thereof, or a coupling of McMurry type starting from the aldehyde,
or via a metathesis starting from the styrene derivative.

The following scheme represents the various routes for obtaining said precursors:

Scheme 1

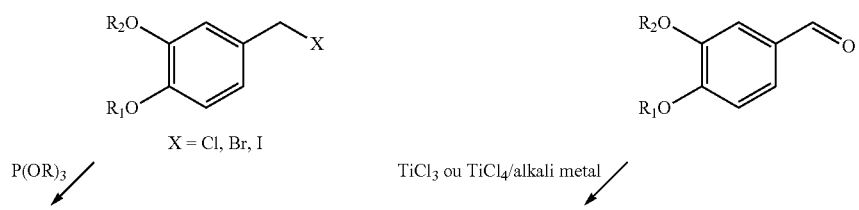

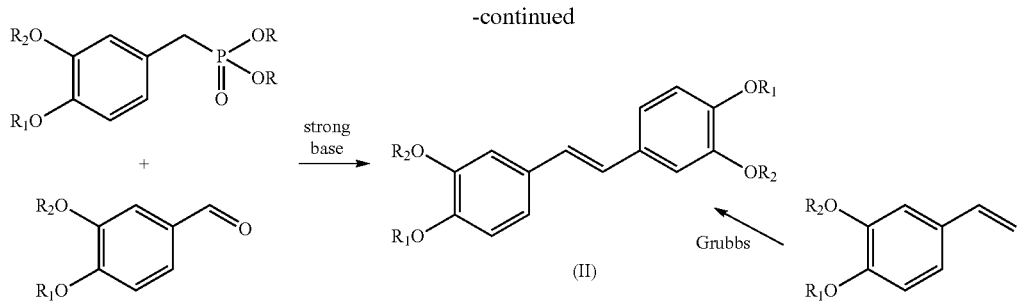

The possible hydroxyl groups of the reagents may, if necessary, be protected beforehand with a suitable protecting group, as reviewed by Peter G. M. Wuts and Theodora W. Greene, in *Greene's Protective Groups in Organic Synthesis*, Fourth Edition, Wiley, 2006.

The full protocol for the synthesis of these compounds, via the three possible types of reaction, is detailed in the experimental section.

Compounds of Formula (Ia)

The compounds of formula (Ia) may be obtained:

either via an epoxidation reaction starting from the ethylenic precursors of formula (II):

two-step reaction starting from the ethylenic derivatives of formula (II), the possible free hydroxyl groups of which are protected beforehand with compatible protecting groups, according to the following scheme:

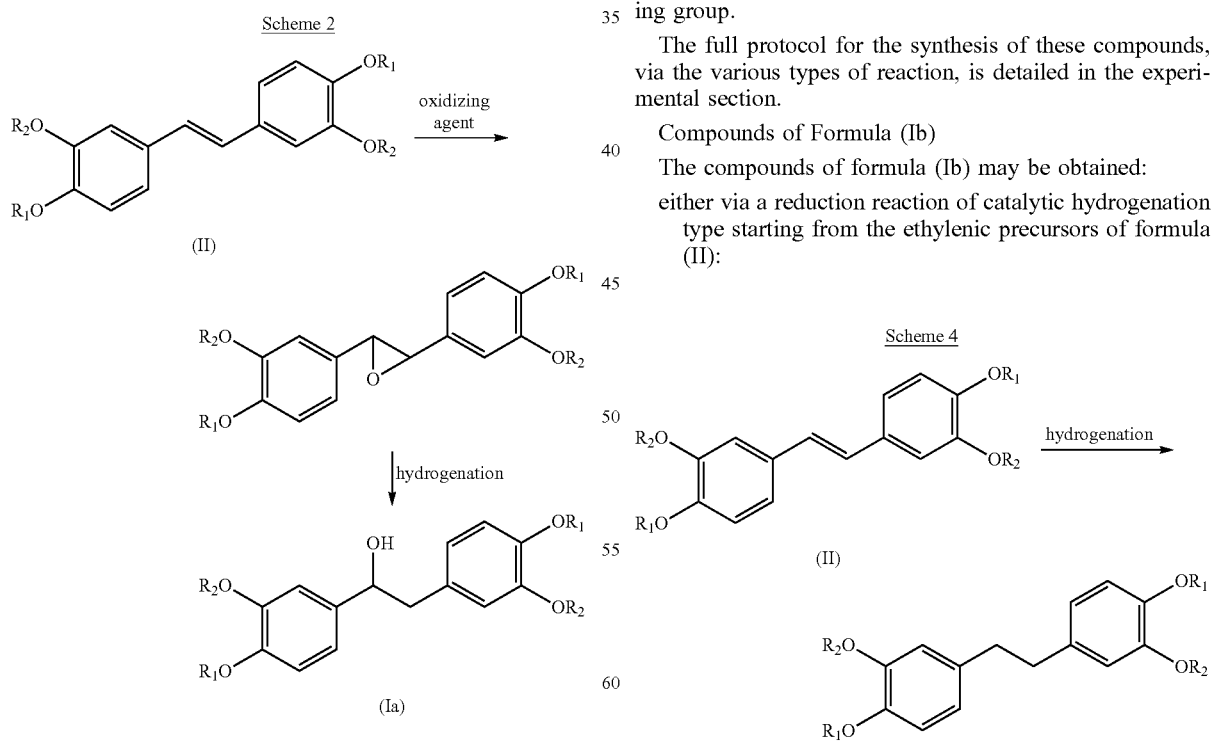

or starting with a halide derivative of a benzyl radical and the aldehyde via a reaction of Nozaki-Hiyama, Grignard or Barbier type, according to the following scheme:

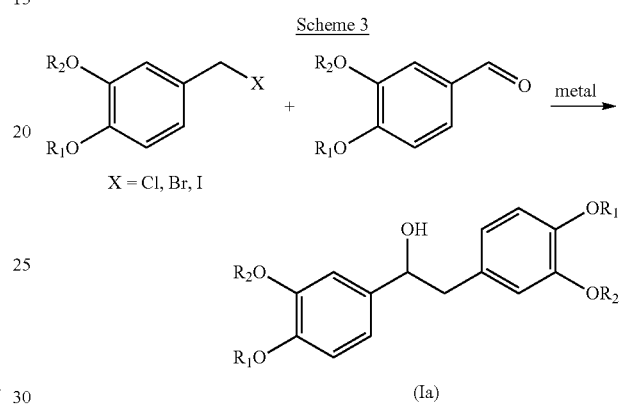

The possible hydroxyl groups of the reagents may, if necessary, be protected beforehand with a suitable protecting group.

The full protocol for the synthesis of these compounds, via the various types of reaction, is detailed in the experimental section.

Compounds of Formula (Ib)

The compounds of formula (Ib) may be obtained:

either via a reduction reaction of catalytic hydrogenation type starting from the ethylenic precursors of formula (II):

or starting from the benzyl halide derivative via a metallo-catalysed coupling reaction of Wurtz or Negishi type:

Scheme 5

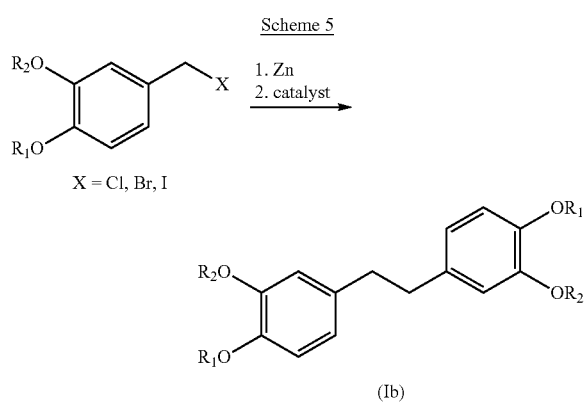

The possible hydroxyl groups of the reagents may, if necessary, be protected beforehand with a suitable protecting group.

The full protocol for the synthesis of these compounds, via the various types of reaction, is detailed in the experimental section.

According to the invention, the compounds of formula (I) may be obtained by a person skilled in the art according to the usual methods. The compounds of formula (I) may also be obtained via the processes specified above.

Cosmetic Composition

The invention relates to a composition, especially a cosmetic composition, comprising, in a physiologically acceptable medium, at least one compound chosen from the compound of formula (I), the compound of formula (Ia), the compound of formula (Ib) and compounds (A) and (B), isomers thereof, salts thereof and solvates thereof as defined in the present description.

It is recalled that a compound of formula (I) covers the compound of formula (Ia), the compound of formula (Ib) and compounds (A) and (B).

The amount of compounds of formula (I) that may be used in the context of the invention obviously depends on the desired effect and must be an amount that is effective for reducing or even inhibiting glycation.

By way of example, the amount of compound of formula (I) may range, for example, from 0.001% to 30% by weight, preferably from 0.01% to 10% by weight and especially from 0.5% to 5% by weight, relative to the total weight of the composition.

The composition according to the invention is especially intended for topical application; it moreover comprises a physiologically acceptable medium, i.e. a medium that is compatible with the skin, including the scalp, mucous membranes, the nails, the hair, the eyelashes, the eyebrows and/or the eyes.

The composition may then comprise any constituent usually used in the envisaged application.

Mention may be made especially of water, solvents, oils of mineral, animal and/or plant origin, waxes, pigments, fillers, surfactants, cosmetic active agents, or polymers.

For example, in the composition according to the invention, the physiologically acceptable medium may comprise at least one cosmetic adjuvant chosen from water; organic solvents, in particular C2-C6 alcohols and C2-C10 carboxylic acid esters; hydrocarbon-based oils, silicone oils, fluoro oils, waxes, pigments, fillers, dyes, surfactants, emulsifiers, cosmetic or dermatological active agents, UV-screening agents, film-forming polymers, hydrophilic or lipophilic gelling agents, thickeners, preserving agents, fragrances, bactericides, odour absorbers and antioxidants.

Also, in the composition according to the invention, the physiologically acceptable medium may comprise at least one compound chosen from: desquamating agents; moisturizers; depigmenting or propigmenting agents; anti-glycation agents; NO-synthase inhibitors; agents for stimulating the synthesis of dermal or epidermal macromolecules and/or for preventing their degradation; agents for stimulating fibroblast and/or keratinocyte proliferation or for stimulating keratinocyte differentiation; muscle relaxants and/or dermo-decontracting agents; tensioning agents; anti-pollution agents and/or free-radical scavengers; agents acting on the capillary circulation; agents acting on the energy metabolism of cells; and mixtures thereof.

Thus, the composition according to the invention may be in the form of an anti-ageing composition, especially a care composition, for combating the outer signs of ageing of the skin.

When the composition of the invention is an emulsion, the proportion of the fatty phase may range from 5% to 80% by weight and preferably from 5% to 50% by weight relative to the total weight of the composition. The oils, emulsifiers and optional coemulsifiers used in the composition in emulsion form are chosen from those conventionally used in the field under consideration. The emulsifier and the coemulsifier are present in the composition in a proportion possibly ranging from 0.3% to 30% by weight and preferably from 0.5% to 20% by weight relative to the total weight of the composition.

This composition may be in any galenical form normally used in the cosmetic and pharmaceutical fields, and may especially be in the form of an optionally gelled aqueous solution, a dispersion, optionally a two-phase dispersion, of the lotion type, an emulsion obtained by dispersing a fatty phase in an aqueous phase (O/W) or vice versa (W/O), or a triple (W/O/W or O/W/O) emulsion or a vesicular dispersion of ionic and/or nonionic type.

The composition of the invention may constitute, for example, a lotion, a gel, a cream or a milk, for example a makeup-removing or cleansing lotion or milk, a shampoo or a shower gel.

A composition suitable for the invention may be in any galenical form normally used in the cosmetics fields.

It may especially be in the form of an aqueous or aqueous-alcoholic solution, which is optionally gelled, a dispersion of the lotion type, which is optionally a two-phase lotion, an oil-in-water or water-in-oil or multiple emulsion, an aqueous gel, a gelled or non-gelled oil, a dispersion of oil(s) in an aqueous phase, especially with the aid of spherules, these spherules possibly being polymer particles or, better still, lipid vesicles of ionic and/or nonionic type, or alternatively in the form of a powder, a serum, a paste or a flexible stick. It may be of solid, pasty or more or less fluid liquid consistency.

Thus, the composition may comprise any constituent usually used in the envisaged topical application and administration.

Mention may be made in particular of water, solvents, oils of mineral, animal and/or plant origin, in particular as detailed hereinbelow, waxes, in particular as described hereinbelow, pigments, fillers, surfactants, thickeners, gelling agents and preserving agents, and mixtures thereof.

A composition that is suitable for use in the invention may also contain various adjuvants commonly used in the cosmetics field, such as sequestrants, odour absorbers, UV-screening agents, fragrances, matt-effect agents, and abrasive fillers or exfoliants, and mixtures thereof.

A composition that is suitable for use in the invention may advantageously comprise at least one additional active agent.

The term "additional active agent" means, in the context of the present invention, a compound which, by itself, i.e. not requiring the intervention of an external agent to activate it, has biological activity which may in particular be:

The additional active agent used in a composition that is suitable for use in the invention may represent from 0.0001% to 20%, preferably from 0.01% to 10% and even better still from 0.01% to 5% by weight relative to the total weight of the composition.

Moreover, a composition that is suitable for use in the invention may advantageously comprise from 5% to 99% by weight and preferably from 35% to 95% by weight of water relative to the total weight of said composition.

Needless to say, a person skilled in the art will take care to select this or these optional additional compound(s), and/or the amount thereof, such that the advantageous properties of the compound of formula (I) according to the invention are not, or are not substantially, adversely affected by the envisaged addition, and such that the properties of the compositions resulting therefrom are compatible with the preferred route of administration.

A composition that is suitable for use in the invention may advantageously comprise at least one fatty phase that is liquid at room temperature and atmospheric pressure.

The amount of oily phase present in the compositions suitable for use in the invention may range, for example, from 0.01% to 50% by weight and preferably from 0.1% to 30% by weight relative to the total weight of the composition.

A composition that is suitable for use in the invention may advantageously be in the form of an emulsion, obtained especially by dispersing an aqueous phase in a fatty phase (W/O) or a fatty phase in an aqueous phase (O/W), of liquid or semi-liquid consistency of the milk type, or of soft, semi-solid or solid consistency of the cream or gel type, or alternatively a multiple emulsion (W/O/W or O/W/O). These compositions are prepared according to the usual methods.

A composition of this type may be in the form of a face and/or body care or makeup product, and may be conditioned, for example, in the form of cream in a jar or of fluid in a tube or in a pump-action bottle.

The emulsions that are suitable for use in the invention may comprise at least one emulsifier chosen from amphoteric, anionic, cationic and nonionic emulsifiers, used alone or as a mixture.

Advantageously, the emulsifiers are appropriately chosen according to the emulsion to be obtained (W/O or O/W). The emulsifiers are generally present in the composition in a proportion that may range from 0.3% to 30% by weight and preferably from 0.5% to 20% by weight relative to the total weight of the composition.

A composition that is suitable for use in the invention may also comprise at least one dyestuff chosen, for example, from pigments, nacres, dyes and materials with an effect, and mixtures thereof.

These dyestuffs may be present in a content ranging from 0.01% to 50% by weight and preferably from 0.01% to 30% by weight relative to the total weight of the composition.

A composition that is suitable for use in the invention may also comprise at least one filler, especially in a content ranging from 0.01% to 50% by weight and preferably ranging from 0.01% to 30% by weight relative to the total weight of the composition.

In the case of oral administration, the composition may be in the form of tablets, gel capsules, sugar-coated tablets, syrups, suspensions, solutions, powders, granules, emulsions, suspensions of microspheres, nanospheres or lipid or polymeric vesicles allowing controlled release. Preferably, the composition is in the form of a food supplement.

In the case of topical administration, the compositions according to the invention may be in the form of products for caring for the skin or semi-mucous membranes, such as a protective, treatment or care composition for the face, for the lips, for the hands, for the feet, for the anatomical folds or for the body (for example, day cream, night cream, makeup-removing cream, makeup base, protective or care body milk, aftersun milk, skincare or scalp-care lotion, gel or foam, serum, powder, mask, artificial tanning composition, aftershave composition, hair composition, product for the region of the armpits, or hygiene and cleansing product).

According to a preferred embodiment, a composition comprising the compound of formula (I) of the invention is formulated in an anti-ageing cream.

A composition according to the invention may be manufactured via any known process generally used in the cosmetics field.

Cosmetic Processes

The present invention also relates to a non-therapeutic cosmetic process for treating the skin, comprising the application to the skin of a composition as defined in the present description.

The present invention also relates to a cosmetic process for treating and/or preventing the onset of the signs of ageing, especially associated with glycation, of the skin, the nails and/or the hair, characterized in that a cosmetic composition as defined in the present description is applied to the skin, the nails and/or the hair.

In certain embodiments of these processes, the composition is applied to mature and/or wrinkled skin.

The non-therapeutic cosmetic process of the invention is performed by topically administering a composition in accordance with the invention.

The topical administration consists of the external application, to the skin, the nails or the hair, of cosmetic compositions according to the usual technique for using these compositions.

By way of illustration, the cosmetic process according to the invention can be performed by application, for example daily, of a composition in accordance with the invention, which may be formulated, for example, in the form of a cream, gel, serum, lotion, emulsion, makeup-removing milk or aftersun composition.

The process according to the invention may comprise a single application.

According to another embodiment, the application is repeated, for example 2 to 3 times daily for one day or more and generally for an extended period of at least 4 weeks, or even 4 to 15 weeks with, where appropriate, one or more periods of stoppage.

Furthermore, treatment combinations optionally with oral or topical forms may be envisaged, in order to complement or to reinforce the activity of a composition as defined by the invention.

Thus, a topical treatment with a composition in accordance with the invention, combined with an oral or topical composition optionally containing a compound of formula (I), might be imagined.

The ingredients are mixed, before being formed, in the order and under conditions that are easily determined by those skilled in the art.

According to a particular embodiment of the invention, other agents intended to make the appearance and/or the texture of the skin more attractive may also be added to the composition according to the invention.

The present invention also relates to the non-therapeutic use of a cosmetic composition as defined previously, for cosmetically preventing and/or treating the signs of ageing of the skin and its appendages.

The invention also relates to the non-therapeutic use of a composition as defined in the present description, for improving the firmness of the skin.

The present invention also relates to the non-therapeutic use of a composition as defined in the present description, for reducing, or even inhibiting, the glycation of proteins of the skin, the nails and/or the hair.

The present invention also relates to the use of a composition as defined in the present description, for reducing, or even inhibiting, the glycation of dermal proteins, in particular of collagen.

The present invention also relates to the use of a composition as defined in the present description, for reducing, or even inhibiting, the glycation of keratins.

Throughout the description, including the claims, the term "comprising a" should be understood as being synonymous with "comprising at least one", unless otherwise specified.

The terms "between . . . and . . . " and "ranging from . . . to . . . " should be understood as being inclusive of the limits, unless otherwise specified.

EXAMPLES

Example 1. Synthesis of the Common Precursors of Formula (II)

The ethylenic precursors of formula (II) may be obtained in various ways, either via an olefination of Wittig type (1) and variants thereof, or via a coupling of McMurry type starting with the aldehyde (2), or via a metathesis starting with the styrene derivative (3), according to the following scheme:

The possible hydroxyl groups of the reagents may, if necessary, be protected beforehand with a suitable protecting group, as reviewed by Peter G. M. Wuts and Theodora W. Greene, in *Greene's Protective Groups in Organic Synthesis*, Fourth Edition, Wiley, 2006.

1.1. Wittig-Horner Reaction

The phosphonate derivative may be obtained from the corresponding benzyl halide via the standard procedures. By way of example, the following protocol may be used:

a mixture of benzyl halide (1 eq.) and of trimethyl or triethyl phosphite (2 eq.) in a high-boiling apolar solvent such as toluene is heated at 110° C. for 4-16 hours.

The product is then purified either by distillation or via standard techniques such as chromatography on a column of silica.

Under anhydrous conditions and under an inert atmosphere, a solution of the phosphonate derivative (1-1.3 eq.) in a polar aprotic solvent such as THF is treated at 0° C. with a strong base (1.1-2 eq.) such as sodium hydride (NaH), lithium diisopropylamide (LDA) or n-butyllithium (BuLi), followed by dropwise addition of a solution of the aldehyde (1 eq.) in the same solvent.

Stirring is continued at room temperature overnight, until the aldehyde has disappeared, and the mixture is then cooled to 0° C.

Water is added dropwise with stirring, followed by dilute aqueous hydrochloric acid solution.

The mixture is then extracted using an organic solvent such as ether, $CH_2Cl_2$ or EtOAc.

The organic phases are combined, dried and concentrated under reduced pressure.

The residue may be purified by chromatography on a column of silica.

1.2. McMurry Reaction

The following protocol may be used for the preparation of the activated titanium:

Under anhydrous conditions and under an inert atmosphere, a mixture of $TiCl_3$ or $TiCl_4$ (5-6 eq.) with a reductive basic metal, such as Li, Mg, Zn, Zn—Cu (10-20 eq.), optionally combined with an arene such as

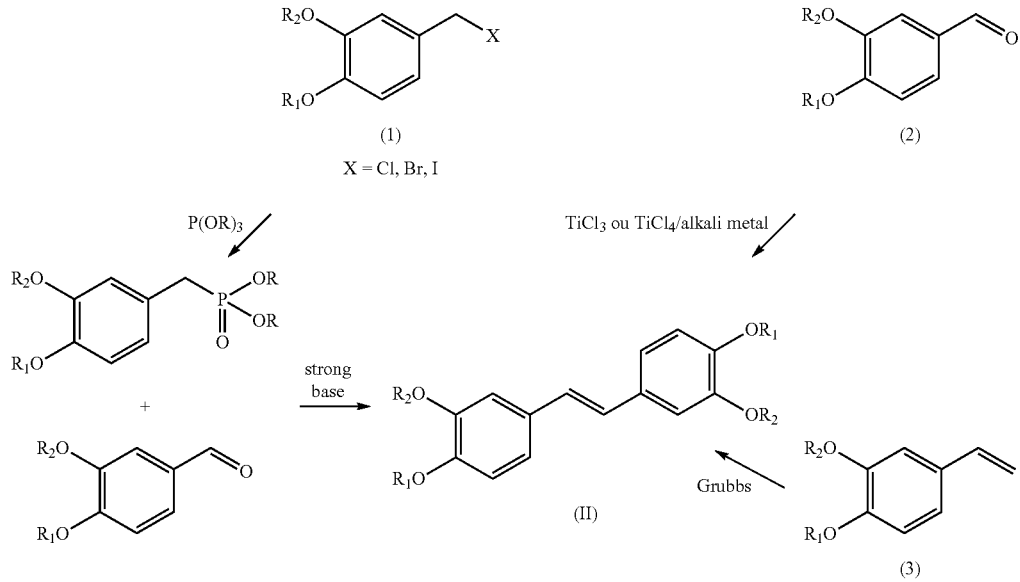

Scheme 1 naphthalene (1 eq.) in a polar aprotic solvent such as THF, is stirred at a temperature of between −5 and 20° C. depending on the procedure.

The coupling step may thus be performed:

To the solution of freshly prepared activated titanium is added the solution of the aldehyde (1-2 eq.) in the same solvent.

The reaction mixture is stirred at room temperature or heated to reflux until the aldehyde has disappeared, and is then neutralized with saturated aqueous NH$_4$Cl solution or 10% K$_2$CO$_3$ solution depending on the procedure, and extracted using an organic solvent such as CH$_2$Cl$_2$ or EtOAc. The organic phases are combined, dried and concentrated under reduced pressure.

The residue may be purified by chromatography on a column of silica.

1.3. Metathesis

The following protocol is applied:

Under anhydrous conditions and under an inert atmosphere, a mixture of a catalyst such as the Grubbs catalyst (1-2 mol %) and of the styrene derivative (1 eq.) in an apolar solvent such as CH$_2$Cl$_2$ is heated to reflux until the styrene has disappeared.

The mixture is then filtered, concentrated under reduced pressure and purified by chromatography on a column of silica.

Example 2. Synthesis of the Compounds of Formula (Ia)

2.1. The compounds of formula (Ia) may be obtained in two steps from the corresponding ethylenic derivatives of formula (II), the possible free hydroxyl groups of which are protected beforehand with compatible protecting groups, according to the following scheme:

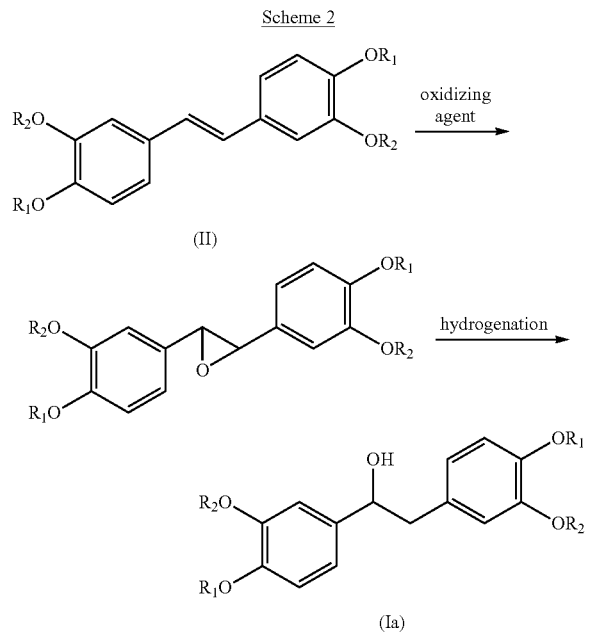

The protocol for the epoxidation of the ethylenic precursors (II) is as follows:

Step 1: Epoxidation

The compound of formula (II) (I eq.) in an apolar solvent such as dichloromethane is treated with an oxidizing agent (1.5-5 eq.) such as mCPBA or H$_2$O$_2$ at room temperature.

The reaction mixture is stirred for 20 hours and then diluted by adding saturated NaHCO$_3$ solution.

After settling, the phases are separated and the aqueous phase is extracted with an organic solvent such as dichloromethane.

The organic phases are combined and then dried.

After evaporating off the solvent, the residue is purified by chromatography on a column of silica.

Step 2: Reduction

The intermediate derived from step 1 (I eq.) is dissolved in a polar solvent such as methanol, ethanol or ethyl acetate.

A heterogeneous catalyst of Pd/C type (5-10 mol %) is suspended in this mixture.

The reaction mixture is stirred at room temperature under an atmosphere of dihydrogen for 1-24 hours.

The catalyst is then removed by filtration and the filtrate is concentrated under reduced pressure.

The residue is purified by chromatography on a column of silica.

The product obtained is then optionally deprotected in a third step.

2.2. The compounds of formula (Ia) may be obtained from the benzyl halide derivative and from the aldehyde via a reaction of Nozaki-Hiyama, Grignard or Barbier type, according to the following scheme:

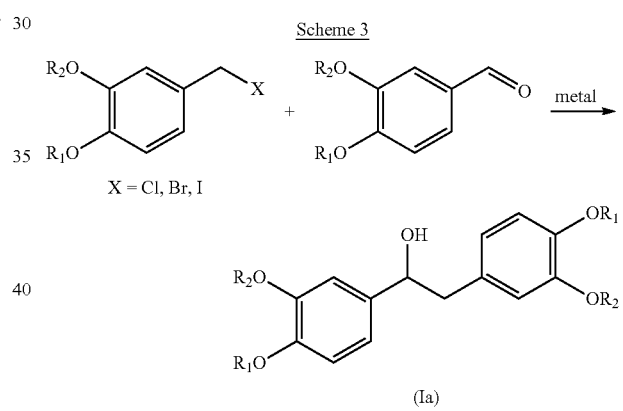

The possible hydroxyl groups of the reagents may, if necessary, be protected beforehand with a suitable protecting group.

2.2.1. Reaction of Grignard Type

Step 1: Preparation of the Grignard Reagent:

Under anhydrous conditions and under an inert atmosphere, magnesium turnings (1.5 eq.) are introduced into a three-necked pear-shaped flask and then heated under vacuum (0.5 mmHg) at 70° C. for 30 min.

The flask is then filled again with argon, and an anhydrous polar aprotic solvent, such as THF or diethyl ether, is added via a syringe, followed by 1,2-dibromoethane (a few drops) to initiate the reaction.

The benzyl halide (1.2-1.3 eq.) in solution in the same solvent is added slowly via a syringe so as to maintain a gentle reflux (15 mL/h).

After the addition, the mixture is refluxed for 2 hours.

Step 2 of Coupling:

In another three-necked round-bottomed flask under anhydrous conditions and under an inert atmosphere, a solution of the aldehyde (1 eq.) in the same solvent or in an apolar solvent such as toluene is cooled to 0° C., then the magnesium solution is added slowly via a syringe or a cannula.

After the addition, the reaction mixture is stirred at between 0 and 20° C. for 2 hours until the aldehyde has disappeared, and then diluted in saturated $NH_4Cl$ solution cooled to 0° C.

The aqueous phase is separated and re-extracted with an organic solvent such as diethyl ether (2×).

The organic phases are combined, washed with saturated NaCl solution, dried and concentrated under reduced pressure.

The residue is purified by chromatography on a column of silica.

The product obtained is then optionally deprotected in a second step.

2.2.2. Reaction of Barbier Type

Zinc powder (2 eq.), $CdCl2$ (1 eq.) and $InCl3$ (0.1 eq.). are added to a mixture of the aldehyde (1 eq.) and of the halide (2 eq.) in water.

The reaction mixture is stirred at room temperature until the reagents have disappeared, and then extracted using an organic solvent such as ethyl acetate (3×).

The organic phases are combined, dried and concentrated under reduced pressure.

The residue is purified by chromatography on a column of silica.

The product obtained is then optionally deprotected in a second step.

2.3. Introduction of the Desired Substituents

The groups incompatible with the key reactions for formation of the target compounds will have to be introduced during a subsequent step according to standard procedures. Similarly, if the reagents are not commercially available, the substituents will have to be introduced onto the corresponding phenolic derivatives, before or after the coupling step, depending on the chemical compatibility.

The reactions described below are common for introducing substituents onto the precursors of formula (II) and the novel compounds of formulae (Ia) and (Ib).

2.3.1. Alkylation/Benzylation of Phenols

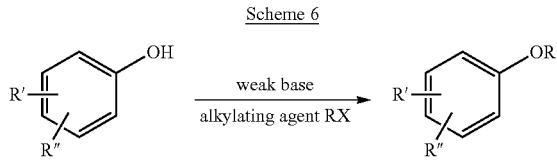

Scheme 6

The following protocol is applied:

The phenolic derivative to be substituted (1 eq./phenol) in a polar aprotic solvent such as DMF or DMSO is deprotonated by adding a weak base (1-2 eq.) such as potassium carbonate or caesium carbonate.

The reaction mixture is stirred at 0-80° C. and the alkylating agent RX (1-2 eq.) is introduced dropwise. For example, the alkylating agent is an alkyl halide and preferentially an alkyl iodide, or benzyl bromide or iodide.

Stirring is continued for 1-96 hours.

The reaction mixture is diluted by adding saturated aqueous $NH_4Cl$ solution and extracted using an organic solvent such as ethyl acetate.

The organic phases are combined, dried and concentrated under reduced pressure.

The residue may be purified by chromatography on a column of silica.

2.3.2. Acylation of Phenols

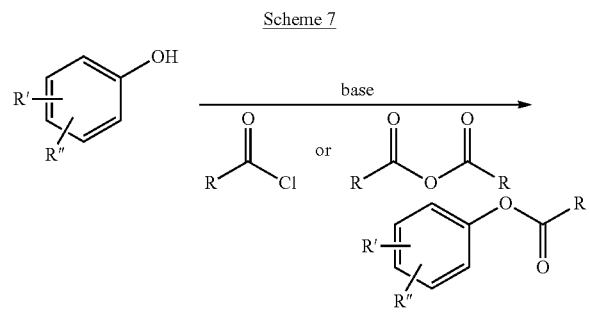

Scheme 7

A solution of the phenolic derivative to be substituted (1 eq./phenol) and of an organic base such as triethylamine, diisopropylethylamine or pyridine (1.2-1.5 eq.), in a polar aprotic solvent such as dichloromethane, acetone, acetonitrile or THF at 0° C., is treated dropwise with a solution of the acid chloride or the corresponding anhydride (1.1-1.5 eq.) in the same solvent.

The reaction mixture is stirred at room temperature for 3-18 hours and then diluted with water.

After settling and phase separation, the organic phase is washed with saturated NaCl solution, dried and concentrated under reduced pressure.

The residue is purified by chromatography on a column of silica.

2.3.3. Carbonatation of Phenols

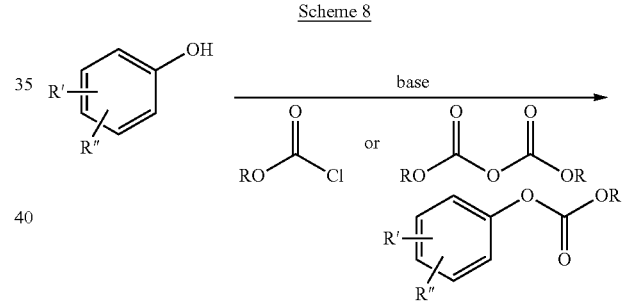

Scheme 8

The procedure is similar to that of the acylation using an alkyl chloroformate or alkyl dicarbonate (1.1-2 eq.).

Example 3. Synthesis of the Compounds of Formula (Ib)

3.1. The compounds of formula (Ib) may be obtained via a reduction reaction starting with the ethylenic precursors of formula (II).

The hydrogenation of the ethylenic derivatives of formula (II) is represented according to the following scheme:

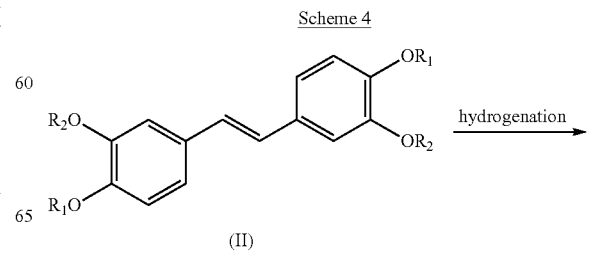

Scheme 4

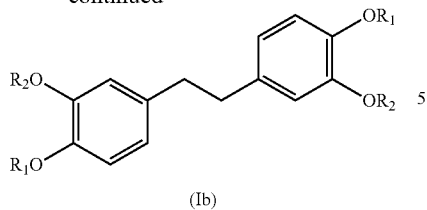

The protocol for the catalytic hydrogenation of the ethylenic precursors (II) is as follows:
- The ethylenic derivative (II) is dissolved in a polar solvent such as methanol, ethanol, THF or ethyl acetate.
- A heterogeneous catalyst of Pd/C or PtO₂ type is suspended in this mixture.
- The reaction medium is stirred at 20-90° C. under dihydrogen (1-40 bar) for 1-24 hours.
- The catalyst is removed by filtration and the filtrate is concentrated under reduced pressure.
- The residue may be purified by chromatography on a column of silica.

The groups incompatible with this reaction, such as the benzyl groups, will have to be introduced during a subsequent step according to standard procedures.

3.2. The compounds of formula (Ib) may be obtained from the benzyl halide derivative via a metallo-catalysed coupling reaction of Wurtz or Negishi type, according to the following scheme:

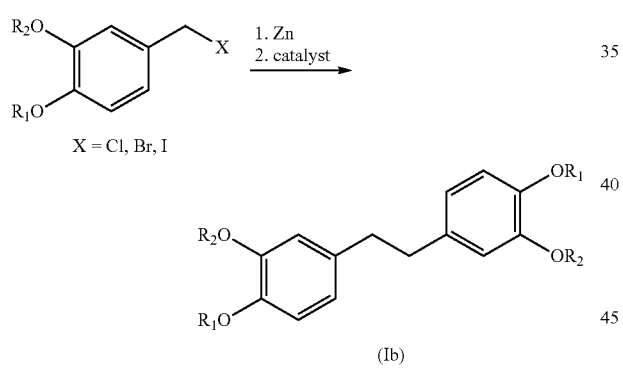

The possible hydroxyl groups of the reagents may, if necessary, be protected beforehand with a suitable protecting group.

The compounds of formula (Ib) may be obtained in particular from the benzyl halide derivative via a Negishi-type reaction, the experimental protocol for which is presented below:

Step 1—Preparation of the Zinc Derivative:
- Under anhydrous conditions and under an inert atmosphere, zinc powder (1.5 eq.) is placed in a pear-shaped Schlenk tube and then heated under vacuum (0.5 mmHg) at 70° C. for 30 min.
- The tube is then filled again with argon, and an anhydrous polar aprotic solvent such as THF, DMA (N,N-dimethylacetamide) or DMI (1,3-dimethyl-2-imidazolidinone), is added via a syringe, followed by iodine (12, 0.025 eq.).
- The reaction mixture is stirred at 70° C. until the red colour turns pale (~5 min).
- The benzyl halide (1 eq.) in solution in the same solvent is added slowly via a syringe.
- The mixture is stirred at 70° C. for 12 hours and then left to cool to room temperature for 1 hour without stirring, in order for the unreacted zinc particles to become deposited at the bottom of the flask.
- The mixture is filtered under argon through a sinter equipped with a two-necked pear-shaped flask in which the solution of the zinc derivative is recovered.

Step 2—Coupling:
- In a three-necked round-bottomed flask, under anhydrous conditions and under an inert atmosphere, a mixture of the catalytic system (catalyst optionally coupled to a ligand), such as NiCl₂.glyme (0.05-0.07 eq.)/ligand of the type Pybox (0.055-0.09 eq.), NiBr₂.diglyme (0.1 eq.)/ligand of the type Pybox (0.13 eq.), Pd₂(dba)₃ (0.02 eq.)/IPr.HCl (0.08 eq.), Pd₂(dba)₃ (0.005 eq.)/tri-o-tolylphosphine (0.02 eq.), or Pd(OAc)₂ (1 mol %)/CPhos (2 mol %), and halogenated derivative (1 eq.) in a polar aprotic solvent such as DMI, DMA, DMF, NMP or THF, is stirred for 5-10 minutes at room temperature, and the organozinc solution (1.2-1.6 eq.) is then added slowly via a syringe or a cannula, while keeping the internal temperature below 0 to 30° C.
- The reaction mixture is stirred at between 0 and 75° C. for 5-24 hours, until the halogenated derivative has disappeared.
- The excess zinc reagent is then neutralized by adding ethanol, and the mixture is diluted with an organic solvent such as diethyl ether.
- This solution is washed with water (3×), dried and concentrated under reduced pressure.
- The residue is purified by chromatography on a column of silica.

The steps for the introduction of the desired substituents are then performed, as presented in Example 2.

Example 4. Biological Activity of Compounds (A) and (B)

Compound A is synthesized, for example, according to the following reference: Synthetic Communications 1987, 17(7), 877-92.

Compound B is synthesized for example according to: Harvery, Benjamin G. et al., Polymer Preprints (American Chemical Society, Division of Polymer Chemistry) 2011, 52(1).

The anti-ageing effect of the compounds of formula (I) is illustrated by the capacity of these compounds (A) and (B) to inhibit the protein glycation activity, according to the conventional test of inhibition of the glycation of bovine serum albumin (or BSA).

A. Materials and Methods

The test compounds are placed in contact with BSA and ribose, and incubation is maintained for 15 days. The fluorescence due to the glycation of BSA by the ribose is measured at T0 and at T15 days. 1 mM aminoguanidine is used as positive control and corresponds to 100% inhibition. The effective doses allowing a 25% inhibition of glycation are determined by means of the dose-response curves.

B. Results

The capacity of each of the compounds of formula (I) A and B to inhibit the glycation of BSA was tested, by means of the test described in the Materials and Methods section.

The results are reported in Table 1 below.

TABLE 1

| compound | IC$_{25}$ | % inhibition at 100 μM |
|---|---|---|
| A | 17 μM | 37% |
| B | 17 μM | 39% |

In Table 1, the IC$_{25}$ value represents the concentration of each compound that induces 25% inhibition of BSA glycation.

Table 1 also presents the percentage values for the inhibition of BSA glycation which is induced by a concentration of 100 μM of each of the indicated compounds.

The results of Table 1 show that the compounds of formula (I) are capable of inhibiting the glycation reaction in the model test.

As active agents in cosmetic formulations, these compounds are thus effective in helping to prevent and/or delay the onset of the signs of ageing that are characteristic of glycation: slackened appearance, flaccid skin, fine wrinkles.

Example 5. Example of Composition in Accordance with the Invention

The percentages of compounds shown are percentages by weight, relatively to the total weight of the composition in which they are present.

| | |
|---|---|
| Compound A | 1% |
| Glycerol | 12% |
| Polyacrylamide at 40% AM* (Sepigel 305 from SEPPIC) | 1% AM* |
| Preserving agents | qs |
| Fragrance | qs |
| Water qs | 100% |

*AM meaning active material

The above composition, applied topically to the skin, makes it possible to combat the signs of ageing, such as wrinkles and fine lines, or also withered, flabby and/or thinned skin.

Example 6: Example of Composition in Accordance with the Invention

The percentages of compounds shown are percentages by weight, relative to the total weight of the composition in which they are present.

| | |
|---|---|
| Compound (A) | 1% |
| Glycerol | 12% |
| Polyacrylamide at 40% AM (Sepigel 305 from SEPPIC) | 1% AM |
| Mixture of polydimethylsiloxane containing α,ω-hydroxyl and cyclopentadimethylsiloxane groups (15/85) | 2% |
| Preserving agents | qs |
| Fragrance | qs |
| Water | qs 100% |

The same types of results are obtained by replacing compound A with compound B.

The invention claimed is:

1. A composition comprising, in a physiologically acceptable medium, at least one compound of formula (I):

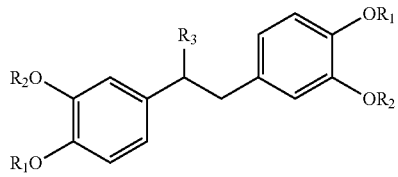

wherein:
  each $R_1$ is independently H;
  each $R_2$ is independently $C_1$-$C_6$ alkyl; and
  $R_3$ is OH;
or a physiologically acceptable salt or stereoisomer thereof,
  wherein the physiologically acceptable medium comprises at least one compound selected from the group consisting of a desquamating agent, a moisturizer, a depigmenting agent, a propigmenting agent, an antiglycation agent, a nitric oxide-synthase inhibitor, an agent for stimulating the synthesis of dermal or epidermal macromolecules, an agent for preventing the degradation of dermal or epidermal macromolecules, an agent for stimulating fibroblast and/or keratinocyte proliferation, an agent for stimulating keratinocyte differentiation, a muscle relaxant, a dermodecontracting agent, a tensioning agent, an antipollution agent, a free-radical scavenger, an agent acting on the capillary circulation, and an agent acting on the energy metabolism of cells, or a mixture thereof.

2. The composition of claim 1, wherein the at least one compound of formula (I) is at least one compound of formula (Ia):

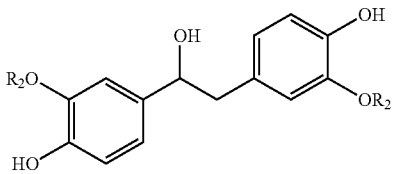

wherein each $R_2$ is independently $C_2$-$C_6$ alkyl.

3. The composition of claim 1, wherein each $R_2$ is independently $CH_3$.

4. The composition of claim 1, wherein the compound of formula (I) is present in an amount of between 0.001% and 30% by weight relative to the total weight of the composition.

5. The composition of claim 1, wherein the physiologically acceptable medium further comprises at least one adjuvant selected from the group consisting of water, an organic solvent, a hydrocarbon-based oil, a silicone oil, a fluoro oil, a wax, a pigment, a filler, a dye, a surfactant, an emulsifier, a cosmetically active agent, a dermatologically active agent, an ultraviolet-screening agent, a film-forming polymer, a hydrophilic gelling agent, a lipophilic gelling agent, a thickener, a preserving agent, a fragrance, a bactericide, an odor absorber, and an antioxidant.

6. The composition of claim 1, wherein the composition is an optionally gelled aqueous solution, a dispersion or an emulsion.

7. A method for cosmetically preventing or treating the onset of the signs of ageing of the skin and the onset of the signs of ageing of the nails in a subject, comprising applying to the skin or the nails of the subject a composition comprising, in a physiologically acceptable medium, at least one compound of formula (I):

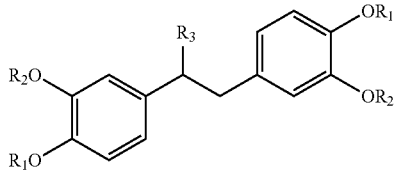

wherein:
  each $R_1$ is independently H;
  each $R_2$ is independently $C_1$-$C_6$ alkyl; and
  $R_3$ is OH;
or a physiologically acceptable salt or stereoisomer thereof,
  wherein the physiologically acceptable medium comprises at least one compound selected from the group consisting of a desquamating agent, a moisturizer, a depigmenting agent, a propigmenting agent, an antiglycation agent, a nitric oxide-synthase inhibitor, an agent for stimulating the synthesis of dermal or epidermal macromolecules, an agent for preventing the degradation of dermal or epidermal macromolecules, an agent for stimulating fibroblast and/or keratinocyte proliferation, an agent for stimulating keratinocyte differentiation, a muscle relaxant, a dermodecontracting agent, a tensioning agent, an antipollution agent, a free-radical scavenger, an agent acting on the capillary circulation, and an agent acting on the energy metabolism of cells, or a mixture thereof.

8. A method for cosmetically preventing or treating the signs of ageing of the skin and the signs of ageing of the nails in a subject, comprising applying to the skin or the nails of the subject a composition comprising, in a physiologically acceptable medium, at least one compound of formula (I):

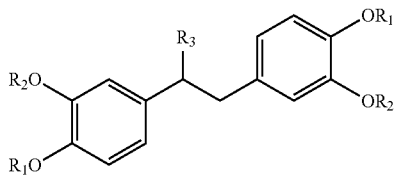

wherein:
  each $R_1$ is independently H;
  each $R_2$ is independently $C_1$-$C_6$ alkyl; and
  $R_3$ is OH;
or a physiologically acceptable salt or stereoisomer thereof,
  wherein the physiologically acceptable medium comprises at least one compound selected from the group consisting of a desquamating agent, a moisturizer, a depigmenting agent, a propigmenting agent, an antiglycation agent, a nitric oxide-synthase inhibitor, an agent for stimulating the synthesis of dermal or epidermal macromolecules, an agent for preventing the degradation of dermal or epidermal macromolecules, an agent for stimulating fibroblast and/or keratinocyte proliferation, an agent for stimulating keratinocyte differentiation, a muscle relaxant, a dermodecontracting agent, a tensioning agent, an antipollution agent, a free-radical scavenger, an agent acting on the capillary circulation, and an agent acting on the energy metabolism of cells, or a mixture thereof.

9. The method of claim 8, wherein each $R_2$ is independently $CH_3$.

10. A method for cosmetically improving the firmness of the skin in a subject, comprising applying to the skin of the subject a composition comprising, in a physiologically acceptable medium, at least one compound of formula (I):

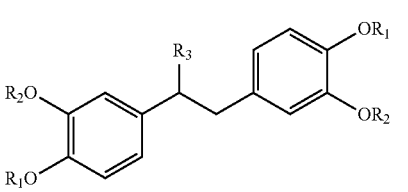

wherein:
  each $R_1$ is independently H;
  each $R_2$ is independently $C_1$-$C_6$ alkyl; and
  $R_3$ is OH;
or a physiologically acceptable salt or stereoisomer thereof,
  wherein the physiologically acceptable medium comprises at least one compound selected from the group consisting of a desquamating agent, a moisturizer, a depigmenting agent, a propigmenting agent, an antiglycation agent, a nitric oxide-synthase inhibitor, an agent for stimulating the synthesis of dermal or epidermal macromolecules, an agent for preventing the degradation of dermal or epidermal macromolecules, an agent for stimulating fibroblast and/or keratinocyte proliferation, an agent for stimulating keratinocyte differentiation, a muscle relaxant, a dermodecontracting agent, a tensioning agent, an antipollution agent, a free-radical scavenger, an agent acting on the capillary circulation, and an agent acting on the energy metabolism of cells, or a mixture thereof.

11. A method for cosmetically inhibiting or reducing the glycation of proteins of the skin and inhibiting or reducing the glycation of proteins of the nails in a subject, comprising applying to the skin or the nails of the subject a composition comprising, in a physiologically acceptable medium, at least one compound of formula (I):

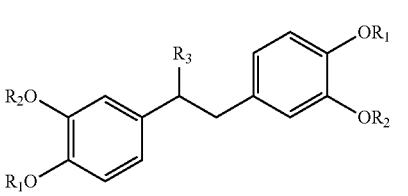

wherein:
  each $R_1$ is independently H;
  each $R_2$ is independently $C_1$-$C_6$ alkyl; and
  $R_3$ is OH;
or a physiologically acceptable salt or stereoisomer thereof,
  wherein the physiologically acceptable medium comprises at least one compound selected from the group consisting of a desquamating agent, a moisturizer, a depigmenting agent, a propigmenting agent, an antiglycation agent, a nitric oxide-synthase inhibitor, an agent for stimulating the synthesis of dermal or epidermal macromolecules, an agent for preventing the degradation of dermal or epidermal macromolecules, an agent for stimulating fibroblast and/or keratinocyte proliferation, an agent for stimulating keratinocyte differentiation, a muscle relaxant, a dermodecontracting agent, a tensioning agent, an antipollution agent, a free-radical scavenger, an agent acting on the capillary circulation, and an agent acting on the energy metabolism of cells, or a mixture thereof.

12. The method of claim 11, wherein the method is for cosmetically inhibiting or reducing the glycation of proteins of the skin.

13. The method of claim 11, wherein the method is for cosmetically inhibiting or reducing the glycation of proteins of the nails.

14. The method of claim 12 or 13, wherein the method is for cosmetically inhibiting or reducing the glycation of keratin.

15. A method for cosmetically treating the skin in a subject, comprising applying to the skin of the subject a composition comprising, in a physiologically acceptable medium, at least one compound of formula (I):

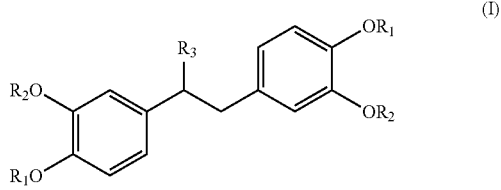

(I)

wherein:
each $R_1$ is independently H;
each $R_2$ is independently $C_1$-$C_6$ alkyl; and
$R_3$ is OH;
or a physiologically acceptable salt or stereoisomer thereof,
wherein the physiologically acceptable medium comprises at least one compound selected from the group consisting of a desquamating agent, a moisturizer, a depigmenting agent, a propigmenting agent, an antiglycation agent, a nitric oxide-synthase inhibitor, an agent for stimulating the synthesis of dermal or epidermal macromolecules, an agent for preventing the degradation of dermal or epidermal macromolecules, an agent for stimulating fibroblast and/or keratinocyte proliferation, an agent for stimulating keratinocyte differentiation, a muscle relaxant, a dermodecontracting agent, a tensioning agent, an antipollution agent, a free-radical scavenger, an agent acting on the capillary circulation, and an agent acting on the energy metabolism of cells, or a mixture thereof.

16. The method of claim 15, wherein the composition is applied to mature skin or wrinkled skin.

* * * * *